(12) United States Patent
Urso

(10) Patent No.: US 9,526,596 B1
(45) Date of Patent: Dec. 27, 2016

(54) DRIVER FOR DENTAL IMPLEMENTS

(71) Applicant: Charles Louis Urso, Waltham, MA (US)

(72) Inventor: Charles Louis Urso, Waltham, MA (US)

(*) Notice: Subject to any disclaimer, the term of this patent is extended or adjusted under 35 U.S.C. 154(b) by 0 days.

(21) Appl. No.: 14/998,713

(22) Filed: Feb. 4, 2016

(51) Int. Cl.
*A61C 17/16* (2006.01)
*A61C 17/22* (2006.01)
*A61C 15/04* (2006.01)
*A46B 13/02* (2006.01)

(52) U.S. Cl.
CPC ............... *A61C 17/22* (2013.01); *A46B 13/02* (2013.01); *A61C 15/047* (2013.01); *A61C 15/048* (2013.01); *A61C 17/16* (2013.01); *A61C 17/225* (2013.01)

(58) Field of Classification Search
CPC ... A61C 17/222; A61C 17/005; Y10T 16/466; Y10T 16/469; A46B 13/02
USPC .......................................................... 15/22.1
See application file for complete search history.

(56) References Cited

U.S. PATENT DOCUMENTS

| | | | | |
|---|---|---|---|---|
| 1,800,254 A | * | 4/1931 | Holmes ................ | B25G 3/02 15/143.1 |
| 2,187,076 A | * | 1/1940 | Erickson ............. | A61C 17/222 15/22.4 |
| 2,187,077 A | * | 1/1940 | Erickson ............. | A61C 17/222 132/73.6 |
| 2,875,458 A | * | 3/1959 | Tsuda ................ | A61C 17/3436 15/176.1 |
| 3,196,299 A | * | 7/1965 | Kott .................. | A61C 17/3481 15/22.1 |
| 3,316,576 A | * | 5/1967 | Urbush ............... | A61C 17/40 15/22.1 |
| 3,497,607 A | | 2/1970 | Swanson | |
| 4,476,604 A | * | 10/1984 | White ................ | A46B 15/0002 15/105 |
| 5,113,037 A | | 5/1992 | King, Jr. et al. | |
| 5,283,921 A | * | 2/1994 | Ng .................... | A61C 17/22 15/145 |
| 5,689,850 A | * | 11/1997 | Shekalim ............ | A61C 17/3436 15/145 |
| 2013/0330122 A1 | * | 12/2013 | Ghasiri ............... | F16F 1/045 403/327 |
| 2016/0076568 A1 | * | 3/2016 | Dilmaghanian ..... | H01R 13/187 403/271 |

* cited by examiner

*Primary Examiner* — Tatiana Nobrega

(57) ABSTRACT

Embodiments shown and described include drivers (11, 50) for power-driving an otherwise manual dental implement (12, 33, 46, 48, 38, 44) of the type including an implement handle attached to a dental hygienic head. One of the drivers (11) comprises a socket (26) defining an entrance (29) for detachably receiving an implement handle within the socket. The socket includes an elongate elastic constrictor (34, 41) positioned to surround the implement handle when the latter is inserted into the socket for holding the dental implement. A motor-powered device (16) connected to the socket is arranged for power-driving the dental implement to facilitate oral hygiene.

9 Claims, 2 Drawing Sheets

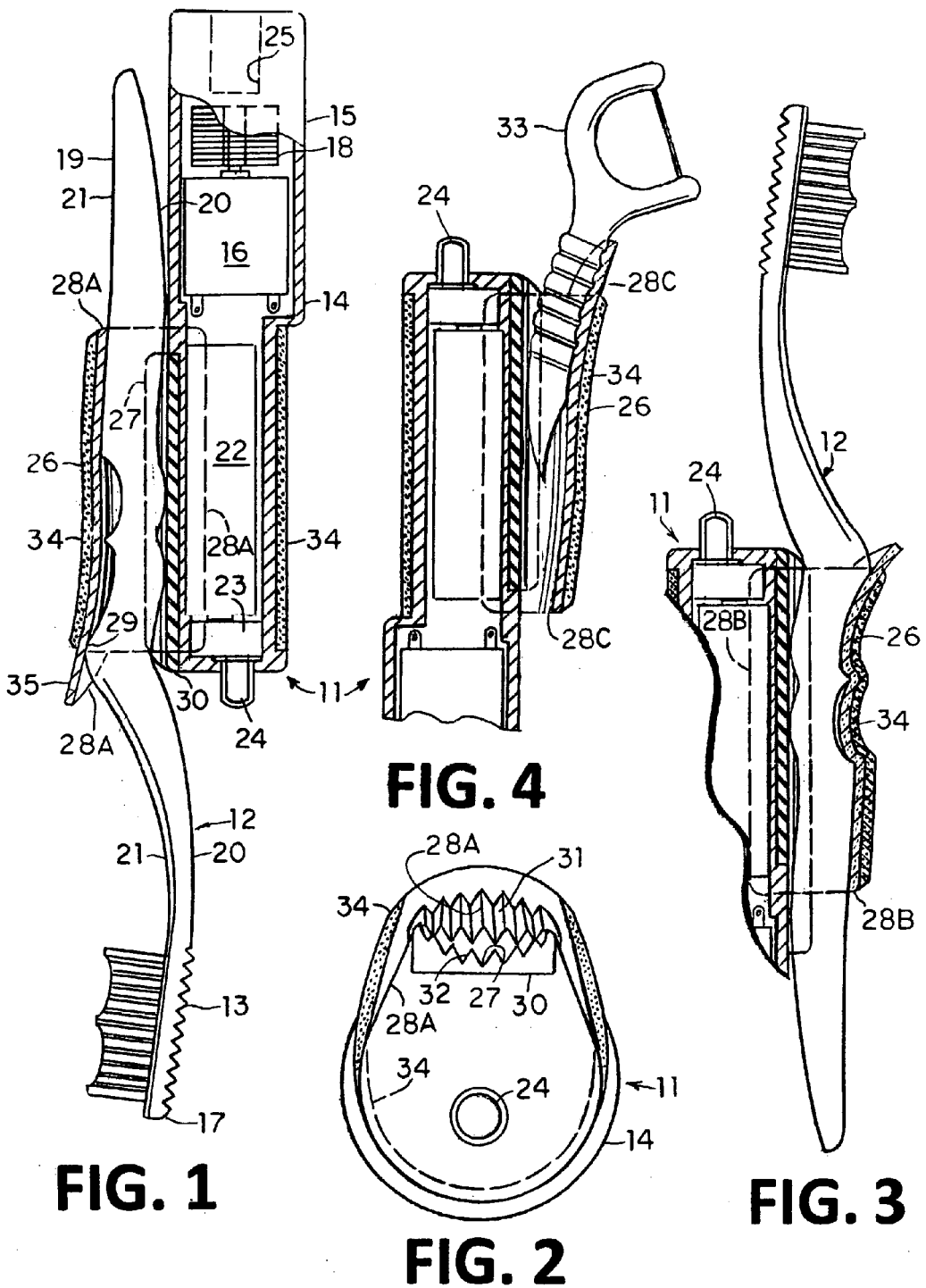

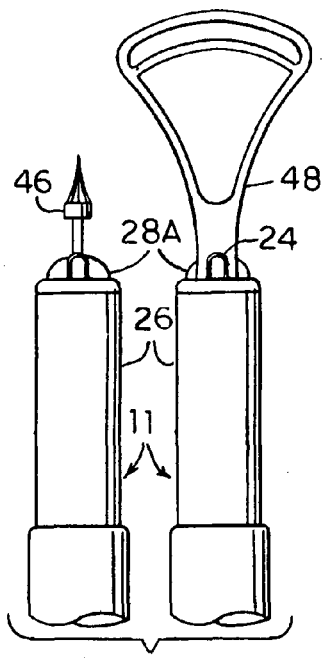
FIG. 5
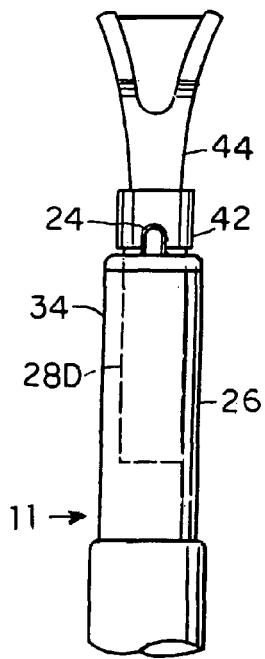
FIG. 9
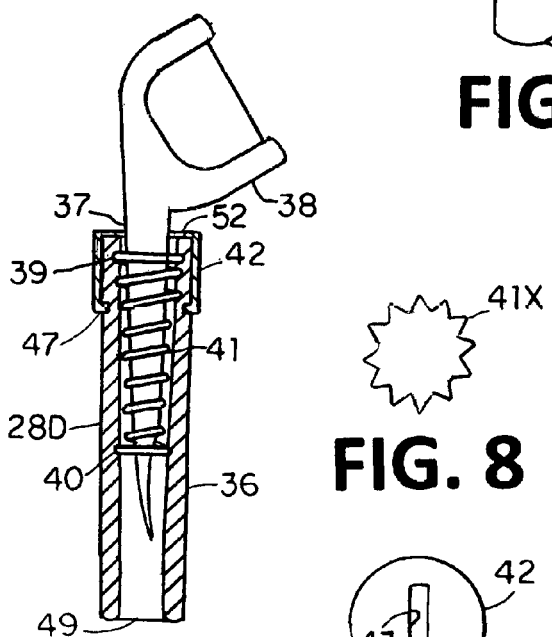
FIG. 6
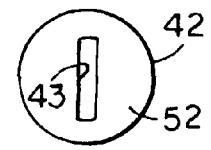
FIG. 7
FIG. 8
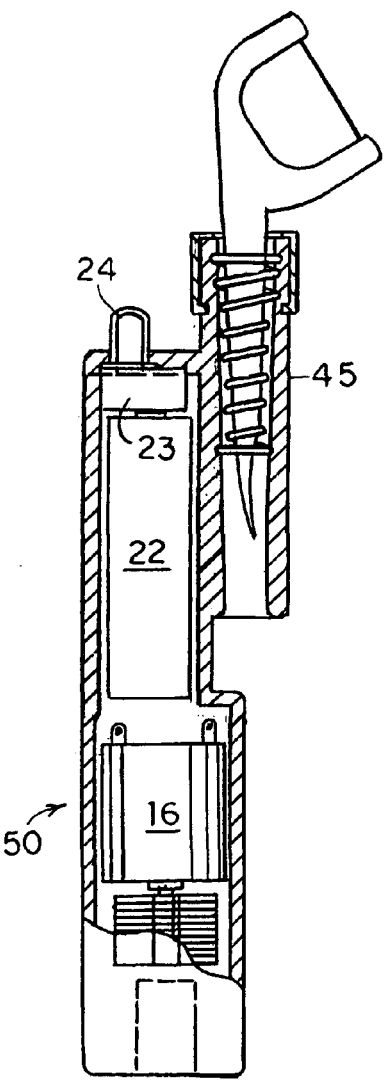
FIG. 10

DRIVER FOR DENTAL IMPLEMENTS

CROSS REFERENCE TO RELATED APPLICATIONS

Not applicable.

BACKGROUND

Eighty percent (80%) of consumers buy manual toothbrushes rather than powered ones. The most compelling reason is the much lower cost of manual toothbrushes in comparison to the high cost of replacement heads for powered toothbrushes. Another probable reason most consumers prefer manual-style toothbrushes is the greater selection including the shape, quantity, feel, and arrangement of the bristles. Moreover, there is a greater availability of manual toothbrushes in comparison to powered toothbrush replacement heads in the most frequently shopped stores.

In addition to the higher cost of replacement brush heads for conventional powered toothbrushes, the replacement brush heads can be difficult to find and may be discontinued. In the latter case, the consumer is left with a useless power-driver. Nevertheless, controlled studies of the cleaning ability of powered versus manual toothbrushes show that the powered ones do a better job by removing more plaque.

With regard to flossing, manual flossing aids called "floss picks" are the most popular and biggest selling flossers. Most types of floss picks are disposable. Each has a tiny plastic toothpick as a handle that is combined with a frame supporting a span of dental floss. Floss picks are intended for manual flossing, but manual flossing is slow, inefficient, and few people can scrub their teeth interdentally by manual means.

Clearly, there is a need for a dental driver that can reduce the cost of oral hygiene by power-driving manual toothbrushes, floss picks, tongue cleaners and more. A further need is for a driver that can facilitate general oral hygiene, including brushing and flossing, comfortably with less work while achieving better results.

SUMMARY OF THE EMBODIMENTS

Embodiments shown and described include a driver for power-driving an otherwise manual dental implement of the type including an implement handle attached to a dental hygienic head such as a floss span supporter, a toothbrush head, or other hygienic aid. The driver comprises a socket defining an entrance for detachably receiving the implement handle within the socket. The socket includes an elongate springy or elastic constrictor serving to surround the implement handle to hold the dental implement. In two of the embodiments, an electric-powered driving device connected to the socket is arranged for power-driving the dental implement to facilitate oral hygiene.

ADVANTAGES OF ONE OR MORE ASPECTS

1. Consumers can power-up common manual dental implements including floss picks, tongue cleaners, and their favorite toothbrushes.
2. Substantially lower cost of power-driving manual dental implements in comparison to the cost of the replacement heads of conventional dental power-drivers.
3. Greater availability and convenience of acquiring and powering manual dental implements in comparison to replacement heads designed to fit a conventional driver.
4. Users avoid the common problem of being left with a useless conventional dental driver because of discontinued models and replacement heads.
5. The simplicity, low cost, and high performance of the embodiments makes them economically and functionally advantages.
6. As a product promoter, one or more embodiments can be customized to drive a particular brand of toothbrushes and/or floss picks.

Other advantages of one or more aspects will be apparent from consideration of the drawings and ensuing description.

DRAWINGS

Closely related components in the figures have the same reference number but different alphabetic suffixes.

FIG. 1 shows a cross-sectional view taken through a longitudinal midline of a driver embodiment wherein the driver includes a socket that holds a manual toothbrush with the aid of a generic insert.

FIG. 2 shows an enlarged front view of the driver of FIG. 1 without the toothbrush to disclose a splined interior of the generic insert in the driver socket.

FIG. 3 shows a fragmental cross-sectional view taken through a longitudinal midline of the driver of FIG. 1 including the toothbrush wherein a second insert made of flexible plastic replaced the generic insert in the driver socket.

FIG. 4 shows a fragmental cross-sectional view taken through a longitudinal midline of the driver of FIG. 1 holding an F-shaped floss pick with the aid of a molded hard plastic third insert customized to conform to the floss pick handle.

FIG. 5, the left drawing shows a fragmental bottom view of the driver of FIG. 1 holding an interdental gum massager, and the right drawing of FIG. 5 shows a fragmental bottom view of the driver of FIG. 1 holding a cheek and tongue cleaner.

FIG. 6 shows a cross-sectional view taken through a longitudinal midline of a detachable floss pick holder or fourth insert that can replace the above-mentioned inserts in the driver socket wherein the fourth insert holds an F-shaped floss pick.

FIG. 7 shows a front view of the detachable floss pick holder of FIG. 6 defining a keyhole-like slot for receiving the handle of a floss pick into the floss pick holder.

FIG. 8 shows an enlarged star-shaped cross-section of wire used to make the helical spring in the detachable floss pick holder of FIG. 6.

FIG. 9 shows a fragmental bottom view of the driver of FIG. 1 wherein the generic insert is replaced by the fourth insert of FIG. 6 holding a Y-shaped floss pick.

FIG. 10 shows cross-sectional view taken through a longitudinal midline of a second embodiment of a driver related to that of FIG. 1 wherein the driver socket is permanently replaced with a version of the insert of FIG. 6.

DETAILED DESCRIPTION

First Embodiment

FIGS. 1-9

A first embodiment is shown in FIGS. 1-9 as driver 11. Referring to FIG. 1, this embodiment can drive dental implements such as a manual-style toothbrush 12 with robust orbital brushing motion. Toothbrush 12 is representative of a conventional manual style and includes a toothbrush head 17, a cheek and tongue cleaner 13, and an elongate handle 19. For orientation, toothbrush 12 has a dorsal side 20 and a ventral side 21.

Driver 11 includes an elongate hollow plastic housing 14. A DC motor 16 is supported in a rear end portion 15 of driver 11. Fixedly mounted on a rear drive shaft of motor 16 is an eccentric weight 18 for being rotated when motor 16 is energized. A rechargeable power cell 22 is electrically connected to energize motor 16 when a momentary power switch 23 is actuated by a power button 24. A flexible membrane covering power button 24 keeps moisture out of housing 14. An electrical circuit (not shown) electrically connecting power cell 22, switch 23, and motor 16 is conventional. Power cell 22 can be charged by way of a conventional base charging peg (not shown) inserted in a peg chamber 25. A conventional battery charging coil (not shown) electrically connected to a conventional battery charging circuit (not shown), enables power cell 22 to be electrically charged.

An elongate socket 26 is supported juxtaposed along driver housing 14 for detachably receiving and holding dental implement handles therein. Socket 26 includes an elongate sulcus or channel 27 along a longitudinal surface of driver housing 14. Channel 27 serves for receiving either the dorsal side 20 or ventral side 21 of toothbrush handle 19 or other handle therein.

A second elongate channel 28A is positioned opposing channel 27 such that the two opposed channels face each other for detachably receiving and holding an implement handle between the channels. Channel 28A is made of molded plastic such as polypropylene. An elastic constrictor comprised of an expandable elastic handgrip 34 movably supports channel 28A and tightly surrounds a front portion of housing 14 including channels 27 and 28A. The front view in FIG. 2 shows that channel 28A is shaped like an upside-down U that straddles channel 27. This arrangement maintains the facing relationship of the channels while being movable relative to each other as implement handles of various sizes and shapes are inserted between the channels.

FIG. 1 shows that an anterior end portion of channel 28A is flared to form a funnel-shaped open entrance portion 29 of socket 26 to facilitate entry of a dental implement handle into socket 26. One of the functions of handgrip 34 is to grip handle 19 to hold toothbrush 12 in socket 26. Being made of stretch silicone, handgrip 34 is also elongate and soft for being comfortably gripped by a user. In addition, handgrip 34 is waterproof and slip-resistant to counter the common wetness often encountered when brushing teeth. Housing 14 is circumferentially indented under handgrip 34 for preventing longitudinal displacement of handgrip 34 and channel 28A.

Channel 28A includes a front end portion forming a thumbnail-shaped thumb tab 35 normally extending out of socket 26. By lifting thumb tab 35, a toothbrush or other implement can be easily removed from socket 26. By pulling thumb tab 35, channel 28A can be drawn out from socket 26 for replacement with one of the specialized inserts described hereinafter. Channel 28A serves as a detachable generic insert or first insert defining an elongate cavity for enclosing a significant portion of any one of a variety of long handles of dental implements such as toothbrush handles within socket 26.

Channel 27 includes a channel bed 30 comprised of thermoplastic elastomer (TPE) overmolded on hard plastic substrate of housing 14. Channel bed 30 serves for at least partially conforming to a dental implement handle, such as toothbrush handle 19, thus helping to inhibit movement of the handle relative to socket 26.

Socket 26 is therefore expandable and comprises a hollow enclosure that includes channels 27 and 28A and defines an open entrance for detachably receiving and securely holding a handle of a dental implement.

As best seen in FIG. 2, each channel 28A and 27 includes a plurality of parallel elongate splines 31 and 32, respectively, arranged in an arcuate cross-sectional pattern. The splines are integrated lengthwise along each channel for slip resistant gripping of an elongate dental implement handle. Each channel 28A and 27 also includes a plurality of V-shaped parallel grooves defined by the splines. Each groove corresponds to a similar groove in the opposite channel, respectively. Each spline points to a corresponding spline on the opposite channel, respectively, and each spline points in a direction that is parallel to the direction pointed by an adjacent spline. The combination of opposed splines and grooves serve for enhanced gripping of dental implement handles that may vary in size and shape.

The left drawing in FIG. 5 shows an interdental gum massager 46 being held in socket 26 with the aid of the generic insert (channel 28A). The right drawing in FIG. 5 shows a cheek and tongue cleaner 48 being held in socket 26 with the aid of the same generic insert. Thus, various types of long-handle dental implements can be held and power-driven by driver 11. This reduces the time and work of practicing oral hygiene while enhancing the results and health benefits.

Second Insert—FIG. 3

FIG. 3 shows socket 26 of driver 11 containing an alternative to channel 28A in the form of a detachable flexible dental implement holder or second insert 28B. Normally shaped similar to channel 28A, this dental implement holder is more easily flexible than channel 28A. Under the urging pressure of elastic handgrip 34, insert 28B at least partially conforms to the handle of a dental implement (toothbrush 12 in this case). Thus, within socket 26, insert 28B is a flexible plastic liner for at least partially conforming to an implement handle. Insert 28B is made of stretch-resistant silicone, but can also work if made from other safe flexible plastic.

Third Insert: A Floss Pick Holder—FIG. 4

FIG. 4 shows the driver of FIG. 1 holding a flosser or floss pick 33 securely within socket 26. Under handgrip 34 is a third insert 28C molded from hard plastic to conform exclusively to the handle of floss pick 33. Power-driving a floss-pick by driver 11 enables fast and efficient flossing, including interdental polishing.

Duel-Function Detachable Floss Pick Holder (Fourth Insert)—FIGS. 6-9

FIGS. 6-9 show a duel-function detachable floss pick holder or fourth insert 28D of driver 11. Referring to FIG. 6, insert 28D includes an elongate tubular socket or housing that forms an elongate ancillary dental implement handle 36. A front entrance is provided for detachably receiving an elongate floss pick handle 37 of a floss pick 38. A rear end entrance 49 of implement handle 36 is open for flushing the hollow interior under a faucet after use. Within implement handle 36 is an elongate elastic constrictor in the form of a helical spring 41 positioned longitudinally therein to receive floss pick handle 37 longitudinally therein. Spring 41 helically surrounds floss pick handle 37 when the latter is inserted into implement handle 36.

Helical spring 41 is tapered and funnel-shaped. More specifically, the overall shape of spring 41 is customized for being shaped approximately like that of a significant portion of a specific floss pick handle; that of floss pick handle 37 in this case.

Spring 41 has open front and rear end portions 39 and 40 fixedly supported by being imbedded in helical grooves within implement handle 36. Between front and rear end portions 39 and 40, the elongate body of spring 41 is suspended for being spaced from the inner surface of implement handle 36 and from all other driver components. The spacing enables spring 41 to adjust its shape to conform more precisely to floss pick handle 37 when received in spring 41. As FIG. 8 indicates, the cross-sectional shape of wire wound to form spring 41 is that of a star 41X to enhance gripping ability.

Referring to FIGS. 6 and 7, a front end portion of implement handle 36 is capped by a tubular cap 42 having a circular front-end plate 52 defining a keyhole-like slot 43 therethrough. Cap 42 is rotatably supported frontally of spring 41 and of implement handle 36 by being rotatably supported on a front end portion of implement handle 36. An inward lip 47 around a posterior edge of cap 42 is received in an annular groove defined around implement handle 36 to retain cap 42 thereon. As arranged, floss pick handle 37 of floss pick 38 passes through slot 43 and through the open front end portion of spring 41 to enter implement handle 36 and spring 41 longitudinally. By being rotatably supported, cap 42 rotatably supports floss pick 38 to be turned like a key (by a user) and thereby screw further into spring 41 to become tightly gripped by the spring. The tight gripping can occur in less than one 360 degree turn. Cap 42 also inhibits lateral movement or bending of floss pick 38. After the floss pick is used for power-flossing, reversing the key-like turn will release the floss pick for disposal. Other floss pick holders can be customized as described above according to the shapes of corresponding floss pick models, respectively.

Implement handle 36 is more ergonomically suitable for manual use of a floss pick than the tiny handle of a conventional floss pick. Thus, insert 28D serves duel functions of being a manual floss pick driver and being an insert portion of driver 11. FIG. 9 shows insert 28D in socket 26 of driver 11 for power-driving a Y-shaped floss pick 44.

Operation of the First Embodiment

Preparation before operation merely requires insertion of one of the inserts in socket 26 followed by insertion of the corresponding dental implement. A user can hold handgrip 34 and press switch button 24 to actuate driver motor 16. The user's fingers holding handgrip 34 are positioned to act as a fulcrum resulting in robust orbital motion of the implement head. Handgrip 34 and switch button 24 are positioned for being close to the implement head for precise user control thereof. Applications include powered flossing, tooth brushing, tongue cleaning, or gum massaging according to the type of implement being used.

Second Embodiment

FIG. 10

FIG. 10 shows a second embodiment 50 devised by replacing socket 26 of driver 11 with a floss pick holder 45 which is a permanently attached version of insert 28D. The components operate as described above for their respective counterparts.

Generic Floss Pick Holder/Driver

I developed generic versions (not shown) of insert 28D and floss pick holder 45 that are similar to those shown and described herein. The funnel-shaped helical spring in each generic version is not customized to a particular floss pick. But the spring is large enough to receive and hold any one of the handles of a plurality of different brands and models of floss picks. The keyhole-like slot in the rotatably supported cap of each generic version is also large enough to receive any one of the different floss pick handles of the mentioned plurality. Thus, the generic versions of insert 28D and of driver 50 can power-drive any one of the plurality of floss pick brands and models.

Conclusion and Scope

From the description and drawings, various other modifications and variations of the driver embodiments can be envisioned. For example, a channel configured like channel 28A, but without splines can be substituted for channel 28A for at least holding toothbrush models. Such a substitute channel can be made of a slip-resistant flexible plastic such as stretch-resistant silicone.

The driver embodiments can hold and drive implements other than those mentioned above. Insert 28D, for example, can be used as an ergonomic manual handle for holding and using interdental brushes. Thus, insert 28D can be packaged as a manual handle with a supply of interdental brushes or packaged with a supply of floss picks.

A hard plastic version of channel 28B (not shown) can be molded to conform exclusively to a particular toothbrush model for driving that model. Thus, the toothbrush model could be promoted as a replacement for both manual and power-driven toothbrushes.

A driver embodiment (not shown) can be devised that permanently includes both socket 26 and floss pick holder 45. By the methods described herein, either or both can be customized for driving particular brands and models of dental implements or be made for generic use of a verity of brands and models.

Thus, the scope of the embodiments should be determined by the appended claims and their legal equivalents rather than by the examples given.

What is claimed is:

1. A driver for power-driving an otherwise manual dental implement of the type including manual toothbrushes and manual floss picks, each implement having an elongate implement handle attached to a dental hygienic head, the driver comprising:
    an elongate socket having an entrance for detachably receiving said implement handle within said socket, said socket including an elastic constrictor in the form of an elongate funnel-shaped helical wire spring having an open front end portion, said spring being positioned in said socket for receiving and constrictively gripping said implement handle after being received through said open front end portion and longitudinally within said spring;
    a cap coupled to the elongate socket at the entrance and being rotatably supported frontally of said front end portion of said spring, said cap defining a through slot for receiving said implement handle enabling rotation thereof with said cap to screw said dental implement further into said spring to become tightly gripped thereby; and
    an electric-powered driving device connected to said socket for power-driving said dental implement to facilitate oral hygiene.

2. The driver of claim 1 wherein said socket includes an elongate channel for receiving said implement handle and at least partially conforming to the shape of said implement handle.

3. The driver of claim 1 wherein said spring has a central portion adjacent said open front end portion and said central portion of said spring is spaced apart from an inner surface of said socket and said electric-powered driving device.

4. The driver of claim 3 wherein the wire forming said helical spring being star-shaped in cross-section to enhance gripping ability.

5. A driver for driving a flosser of the type including an elongate flosser handle attached to a flossing frame for supporting a span of dental floss, the driver comprising:
   an elongate socket having an entrance for detachably receiving said flosser handle, said socket enclosing an elongate funnel-shaped helical spring for helically surrounding said flosser handle when inserted into said socket, said spring including a front end portion attached to said socket;
   a cap coupled to said socket at said entrance and being rotatably supported frontally of said front end portion of said spring, said cap defining a keyhole-like slot for receiving said flosser handle enabling rotation thereof with said cap to screw said flosser further into said spring to become tightly gripped thereby; and
   an electric-powered driving device connected to said socket for power-driving said flosser to facilitate dental flossing.

6. The driver of claim 5 wherein said spring has a central portion adjacent said open front end portion and said central portion of said spring is spaced apart from an inner surface of said socket and said electric-powered driving device.

7. A method for producing a floss pick driver for ergonomically driving a floss pick of the manual type including an elongate floss pick handle attached to a flossing frame supporting a span of dental floss, the method comprising:
   a. providing an elongate hollow ancillary handle having a front entrance for detachably receiving said floss pick handle;
   b. providing an elongate funnel-shaped helical wire spring having an open front end portion;
   c. providing a cap having a slot therethrough;
   d. attaching said spring longitudinally within said ancillary handle such that the open front end portion of said spring is toward the front entrance of said ancillary handle and attaching said cap to an end portion of said ancillary handle frontally of said open front end portion such that the cap is rotatably supported in front of the spring whereby said floss pick handle can be inserted through said slot to extend longitudinally through the interior of said spring such that said spring helically surrounds said floss pick handle when inserted into said ancillary handle and said cap rotatably supports said floss pick so that the latter can be turned like a key to screw said floss pick handle further into said spring to become tightly gripped thereby; and
   e. providing an electric-powered driving device coupled to said hollow ancillary handle for power-driving said floss pick.

8. The method of claim 7 wherein said spring has a central portion adjacent said open front end portion and said central portion of said spring, said method further comprising arranging said central portion to be spaced apart from an inner surface of said socket and said electric-powered driving device.

9. The method of claim 7 further comprising arranging for the cross-sectional shape of the wire forming said helical spring as being star-shaped to enhance gripping ability.

\* \* \* \* \*